United States Patent [19]

Marple

[11] 4,133,202
[45] Jan. 9, 1979

[54] MULTIPLE NOZZLE SINGLE STAGE IMPACTOR

[75] Inventor: Virgil A. Marple, Minneapolis, Minn.

[73] Assignee: The Regents of the University of Minnesota, Minneapolis, Minn.

[21] Appl. No.: 789,815

[22] Filed: Apr. 22, 1977

[51] Int. Cl.² .......................................... G01N 15/02
[52] U.S. Cl. .................................. 73/28; 73/432 PS; 55/270
[58] Field of Search ............ 73/28, 421.5 R, 421.5 A, 73/432 PS; 55/270, 484; 209/1

[56] References Cited

U.S. PATENT DOCUMENTS

| | | | |
|---|---|---|---|
| 2,894,877 | 7/1959 | Sinden | 73/28 X |
| 3,678,759 | 7/1972 | Schneeberger | 73/432 PS |
| 3,983,743 | 10/1976 | Olin et al. | 73/28 |

FOREIGN PATENT DOCUMENTS 278,967  6/1971  Russian .................................... 73/28

Primary Examiner—James J. Gill
Attorney, Agent, or Firm—Burd, Braddock & Bartz

[57] ABSTRACT

A single stage impactor having a plurality of different sized nozzles that predicate a particle collection efficiency curve that approximates a predetermined curve. The impactor has a particle collection plate mounted on a casing having a passage connected to an air moving device. A nozzle plate having a plurality of different sized nozzles is mounted on the collection plate. The nozzles can be round, rectangular, or a combination of round and rectangular. The sizes of the different nozzles are coordinated with the pressure drop across the nozzle plate to provide the nozzles with different particle collection cut-off characteristics. The combined collection efficiency curve or penetration curve of all of the different sized nozzles approximates a predetermined curve, as a respirable particle penetration curve.

90 Claims, 21 Drawing Figures

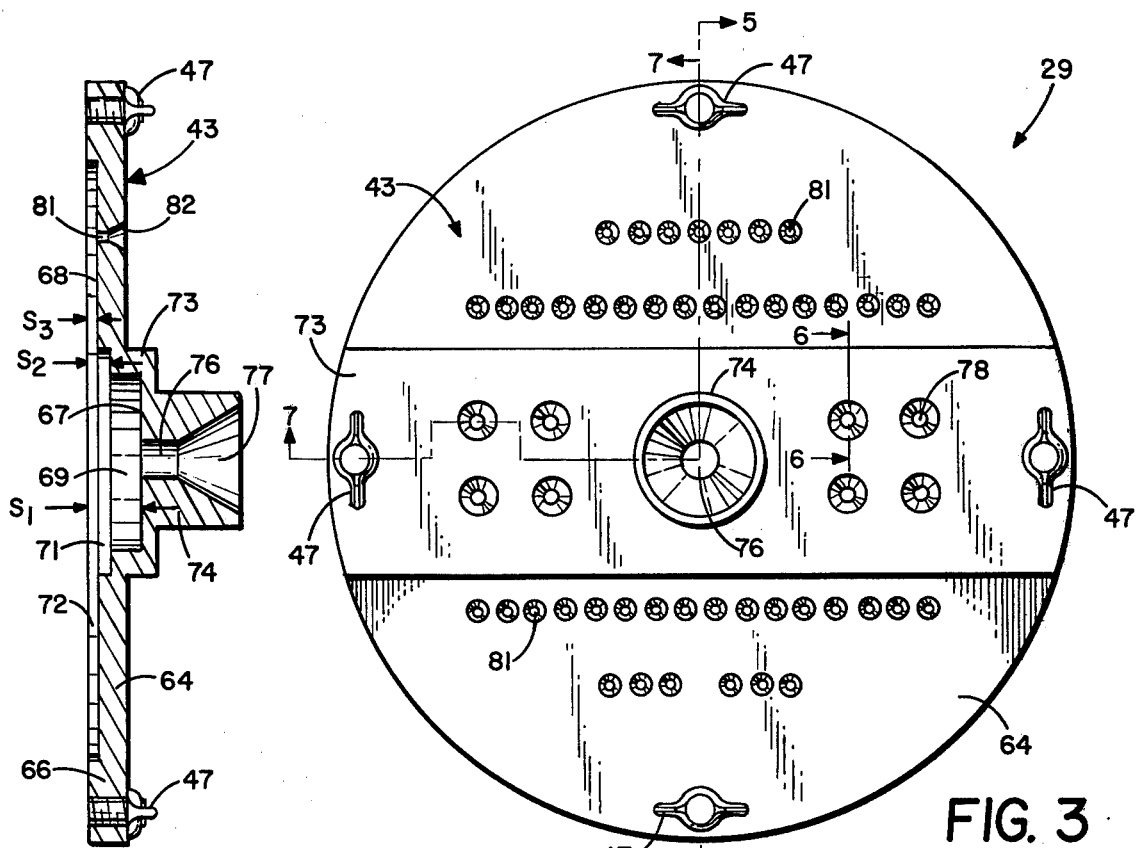
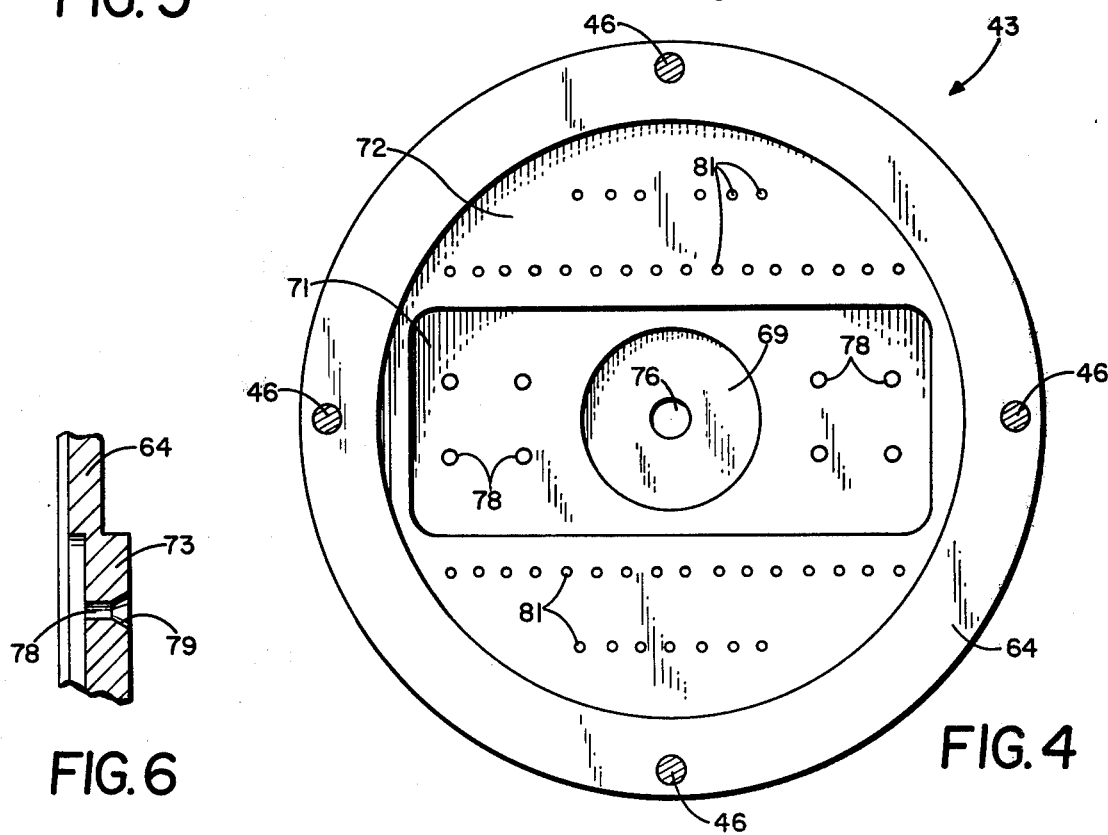

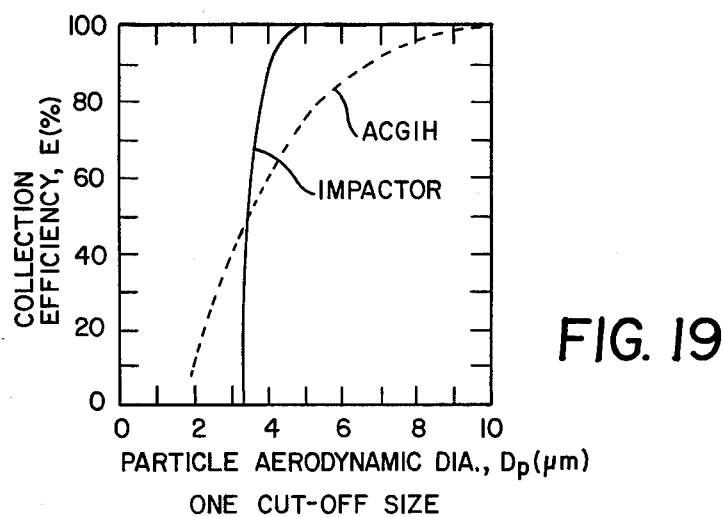
FIG. 19 ONE CUT-OFF SIZE
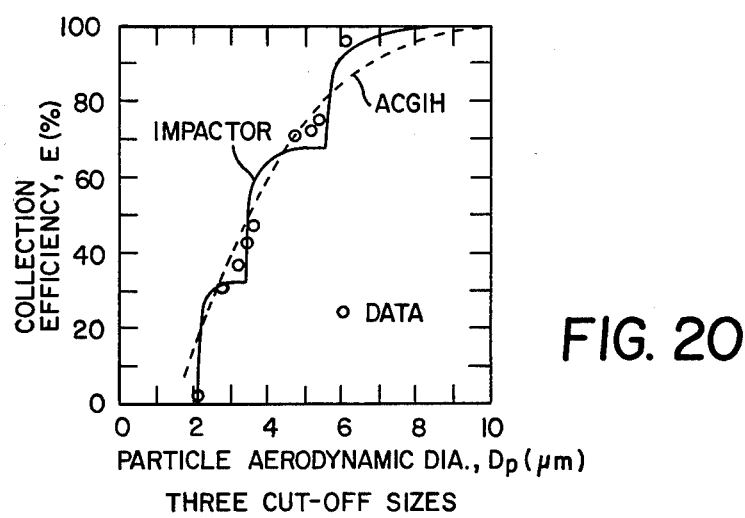
FIG. 20 THREE CUT-OFF SIZES
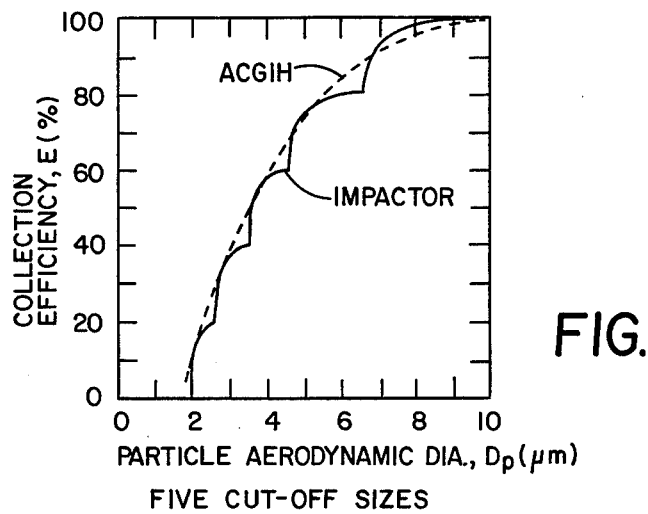
FIG. 21 FIVE CUT-OFF SIZES

MULTIPLE NOZZLE SINGLE STAGE IMPACTOR

BACKGROUND OF THE INVENTION

Figure 1:
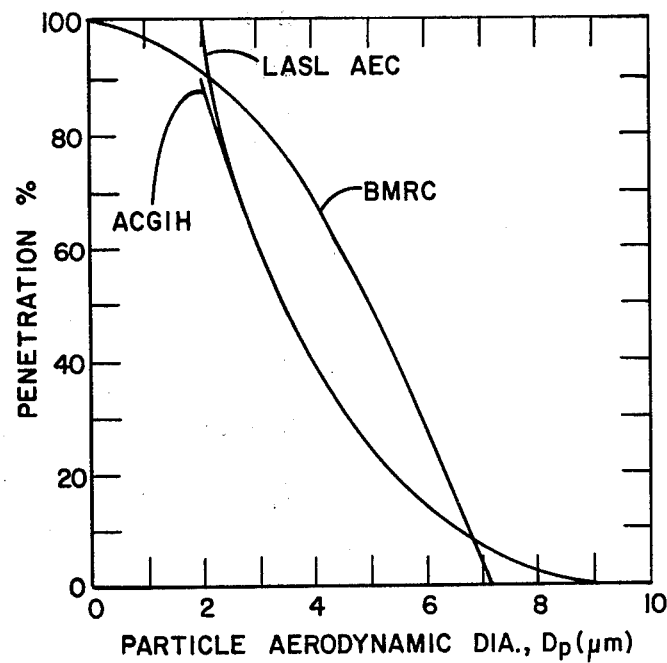
Figure 2:
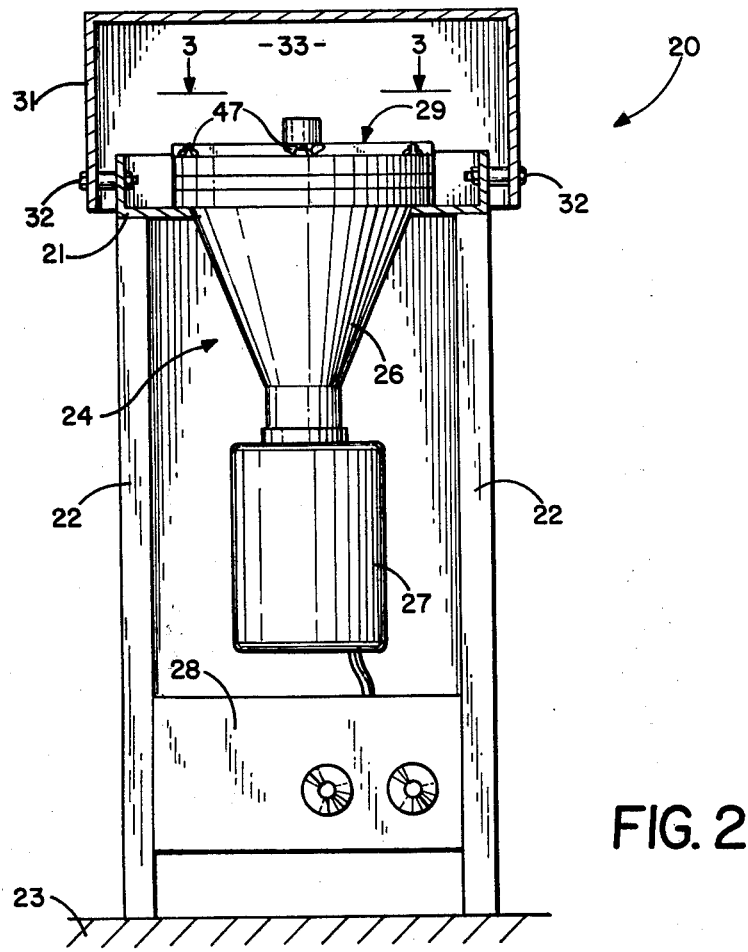

The quantity of respirable aerosol particles is an important factor in the determination of the inhalation hazards of aerosol particles. Primate and animal nasal passages have structures and hair that allow inertial mechanisms to remove aerosol particles from the air moving in these passages. The aerodynamic diameter size distribution of aerosol particles in the nasal passage is determinative of the quantity of respirable aerosol particles. The relationship between the percentage of penetration of the aerosol particles to the respiratory tract and the particle aerodynamic diameter has been determined by several organizations such as the British Medical Research Council (BMRC), the U.S. Atomic Energy Commission (AEC), and the American Conference of Governmental Industrial Hygienists (ACGIH). These relationships are represented in the graph of FIG. 1. FIG. 1 indicates that the penetration to the respiratory tract decreases from about 100% at $2\mu$ to about 0% at $10\mu$ aerodynamic diameter.

The quantity of respirable particles in an aerosol can be found from one of two general methods. One method is to measure the particle size distribution of the entire aerosol, and then apply one of the penetration curves of FIG. 1 to the resultant size distribution. The other method is to pass the aerosol through a size classification device which has a penetration curve similar to one of the curves in FIG. 1, and analyze the particles which penetrate the classification device.

Two size classification devices have been commonly used to approximate the respirable penetration curves. These devices are the horizontal elutriator and the cyclone. The penetration characteristics of the elutriator is determined by physical theory. The penetration characteristics of the cyclone is determined experimentally.

Another sampling device which classifies particles by their aerodynamic size is the inertial impactor. Impactors have been used as respirable preseparators. They have not found wide acceptance because their cut-off characteristics are much sharper than the respirable penetration curves. For example, the single cut-off size impactor collector efficiency is much steeper than the ACGIH curve as shown in FIG. 19. An advantage of an impactor is that the particle collection characteristics can be predicted. They are also compact in structure, operate in any position, and are simple to construct.

Theoretical analysis techniques have been developed so that the fluid flow field and the characteristic particle collection efficiency curve, or penetration curve, of inertial impactors of both round and rectangular nozzles can be accurately predicted. Experimental investigations have shown that these theoretically predicted collection efficiency curves agree well with experimentally determined efficiency curves.

The 50% particle cut-off size $D_{P50}$, of an impactor (i.e., the particle size at which 50% are collected and 50% penetrate) is governed by a particle collection criteria as represented in the following equation:

$$D_{P50} = \left[ \frac{9\mu \, W \, Stk_{50}}{\rho_p \, C \, V_o} \right]^{\frac{1}{2}} \tag{1}$$

where
$\mu$ = absolute air viscosity
$W$ = nozzle diameter (round impactor) or nozzle width (rectangular impactor)
$Stk_{50}$ = Stokes number corresponding to 50% particle collection
$C$ = Cunningham slip correction
$V_o$ = average velocity in nozzle = flow rate/nozzle area Variations of the components of equation (1) can be made without substantially altering particle collection characteristics.

The value of $Stk_{50}$ is a function of the Reynolds number of the flow in the impactor nozzle, Re, and of the dimensionless parameters S/W and T/W, where S = jet-to-plate distance and T = throat length. The influence of these three parameters on the value of $Stk_{50}$ has previously been published. "Characteristics of Laminar Jet Impactors", Marple and Liu, *Environmental Science and Technology*, Vol. 8, No. 7, pp. 648-654, July 1974. This work shows that if the impactor is designed such that S/W > 1.0 (round impactor) or S/W > 1.5 (rectangular impactor) and T/W > ¼, their influence on $D_{P50}$ will be small. Thus, the Reynolds number, defined as $$Re = \frac{\rho \, W \, V_o}{\mu} \quad \text{(round nozzle)} \tag{2}$$

$$Re = \frac{\rho \, 2W \, V_o}{\mu} \quad \text{(rectangular nozzle)} \tag{3}$$

where $\rho$ = the air density, will then be the major parameter in defining the value of $Stk_{50}$ and the shape of the collection efficiency curve.

Another consideration in the analysis of impactors is that the pressure drops, $\Delta P$, across the impactor nozzle is approximately equal to the dynamic pressure of the air jet in the nozzle, $$\Delta P = \tfrac{1}{2} \rho V_o^2 \tag{4}$$

Additional reference is made to the publication "On Fluid Flow and Aerosol Impaction in Inertial Impactors", *Journal of Colloidal and Interface Science*, Vol. 53, No. 1, October 1975, pp. 31-34, Marple and Liu.

High volume sampling apparatus and personal samplers are used for sampling of suspended particles in outdoor and occupational environments. Air pollution and occupational health monitoring are concerned with aerosol particles which size is within the respirable range, i.e., less than 8 to 10 microns. Aerosol particles of this size upon inhalation by humans enter and are retained by the respiratory tract and lungs. Particles larger than the respirable range generally do not constitute a health hazard, although they may cause soiling, corrosion, and other adverse environmental effects. The standard high volume air sampler collects essentially all particles which reach its surface. These particles fall within the size range from about 0 to 100 microns. This sampler does not per se permit an analysis of the respirable particles. Cascade impactors are used with this type of sampler to obtain particle size distribution data. An example of this impactor is disclosed by Anderson in U.S. Pat. Nos. 3,011,914 and 3,795,135.

SUMMARY OF THE INVENTION

A single stage impactor unit has a collection efficiency curve that approximates a predetermined curve, as a respirable penetration curve. The impactor unit has a casing having an open inlet end and a passage for carrying air through the casing. An air moving means, as a blower, mounted on the casing is operable to move air through the passage. An impactor plate having a plurality of openings is located on the casing. The impactor plate has a plurality of particle collecting surfaces for collecting aerosol particles. The aerosol particles that are not collected on the surfaces penetrate through the impactor unit. A nozzle plate is located over and mounted on the impactor plate. The nozzle plate has a plurality of openings, as holes and slots of different sizes aligned with the particle collecting surfaces of the impactor plate. The cut-off characteristics of different sized openings determines the size range of particles that are collected on the particle collecting surfaces. The sizes of the openings are correlated with each other so that the combined collection efficiency curve of all of the openings approximates a predetermined curve, such as one of the respirable penetration curves shown in FIG. 1.

An object of the invention is to provide a single stage multiple-nozzle impactor unit having particle collection characteristics that approximates a predetermined particle collection curve, such as a known respirable collection curve. A further object of the invention is to provide a single stage impactor with a plurality of different sized openings having different particle cut-off characteristics. A further object of the invention is to provide a single stage multiple-nozzle impactor unit having predetermined penetration characteristics that can be readily constructed and is reliable and efficient in use. A further object of the invention is to provide single stage plural nozzle impactor units usable as a personal sampler to monitor respirable aerosol particles. These and other objects and advantages of the impactor unit of the invention are shown and described in the following disclosure.

IN THE DRAWINGS

FIG. 1 is a graph showing the respirable penetration curve of aerosol particles as determined by the British Medical Research Council (BMRC), the Atomic Energy Commission (AEC), and American Conference of Governmental Industrial Hygienists (ACGIH);

FIG. 2 is an elevational view partly sectioned of a high volume sampling apparatus;

FIG. 3 is an enlarged top plan view referenced along the line 3—3 of FIG. 2 looking in the direction of the arrows;

FIG. 4 is a bottom plan view of FIG. 3;

FIG. 5 is a sectional view taken along the line 5—5 of FIG. 3;

FIG. 6 is a sectional view taken along the line 6—6 of FIG. 3;

FIG. 7 is a sectional view taken along the line 7—7 of FIG. 6;

FIG. 8 is a sectional view taken along the line 8—8 of FIG. 7;

FIG. 9 is a top plan view of a modification of the sampling apparatus;

FIG. 10 is a sectional view taken along the line 10—10 of FIG. 9;

FIG. 11 is a sectional view taken along the line 11—11 of FIG. 9;

FIG. 12 is a top plan view of a third modification of the sampling apparatus;

FIG. 13 is a sectional view taken along the line 13—13 of FIG. 12;

FIG. 14 is a top plan view of a fourth modification of the sampling apparatus;

FIG. 15 is a sectional view taken along the line 15—15 of FIG. 14;

FIG. 16 is an enlarged sectional view taken along the line 16—16 of FIG. 14;

FIG. 17 is an enlarged sectional view taken along the line 17—17 of FIG. 14;

FIG. 18 is a sectional view taken along the line 18—18 of FIG. 15;

FIG. 19 is a comparison of theoretical particle collection efficiency curve for impactor with one cut-off size with the ACGIH respirable curve;

FIG. 20 is a comparison of theoretical particle collection efficiency curve and experimental data for impactor with three cut-off sizes with the ACGIH respirable curve; and FIG. 21 is a comparison of theoretical particle collection efficiency curve for impactor with five cut-off sizes with the ACGIH respirable curve.

DETAILED DESCRIPTION OF PREFERRED EMBODIMENTS

Referring to FIG. 2, there is shown a high volume sampling apparatus or instrument of the invention, indicated generally at 20, having aerosol particle collection characteristics that approximate one of the respirable penetration curves of FIG. 1. Apparatus 20 has a generally box-shaped frame 21 attached to a plurality of downwardly directed legs or supports 22. The lower ends of legs 22 engage a supporting surface such as the ground 23. A sampler indicated generally at 24 is mounted on frame 21. Sampler 24 has a downwardly directed tubular housing or casing 26 carrying an air moving means, such as a blower 27. Blower 27 includes an electric motor and fan or vane structure operable to move air through casing 26. A control unit 28 secured to legs 22 is operably connected to blower 27. Control unit 28 includes motor speed controls as well as controls for timing the operation of the motor.

An impactor unit indicated generally at 29 is mounted on top of casing 26. An inverted box-shaped cover 31 is located over frame 21. A plurality of mounts 32 pivotally support cover 31 on frame 21. Cover 31 is larger than frame 21 and surrounds a space or chamber 33 which allows air and aerosol particles entrained in the air to flow to impactor unit 29.

Referring to FIG. 7, casing 26 has a downwardly directed funnel-shaped passage 34 leading to blower 27. The upper edge of casing 26 has an outwardly directed peripheral lip 36. The inner edge of lip 36 has a circular shoulder 37 providing a supporting ledge or surface for a filter indicated generally at 38. Filter 38 has an outside or outer peripheral frame 39 supported on shoulder 37. Frame 39 surrounds and is secured to a filtering media 41 which collects the aerosol particles that pass through an opening in an impactor plate indicated generally at 42. The filter after the test is completed is analyzed to determine properties and chemistry of the collected particles. The analysis can be chemical, X-ray diffraction and weight. Other instruments in lieu of the filter can be used to measure the size, size distribution and amounts of particles that pass through the impactor plate. These instruments can be an aerosol mass monitor, optical particle counter, and cascade impactor.

A multiple-nozzle plate, indicated generally at 43, is located over impactor plate 42. Lip 36 and plates 42 and 43 have aligned vertical holes 44. A plurality of upwardly directed bolts 46 extend through holes 44. Wing nuts 47 on bolts 46 clamp the plates 42 and 43 to lip 36. Wing nuts 47 are removable so that the impactor plate 42 and nozzle plate 43, as well as the filter 38, can be removed from casing 26.

Figure 7:
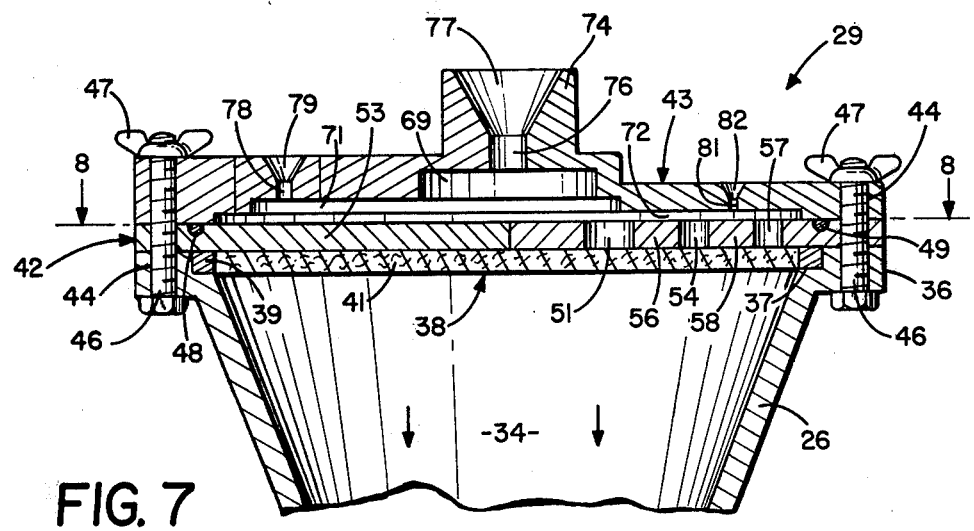
Figure 8:
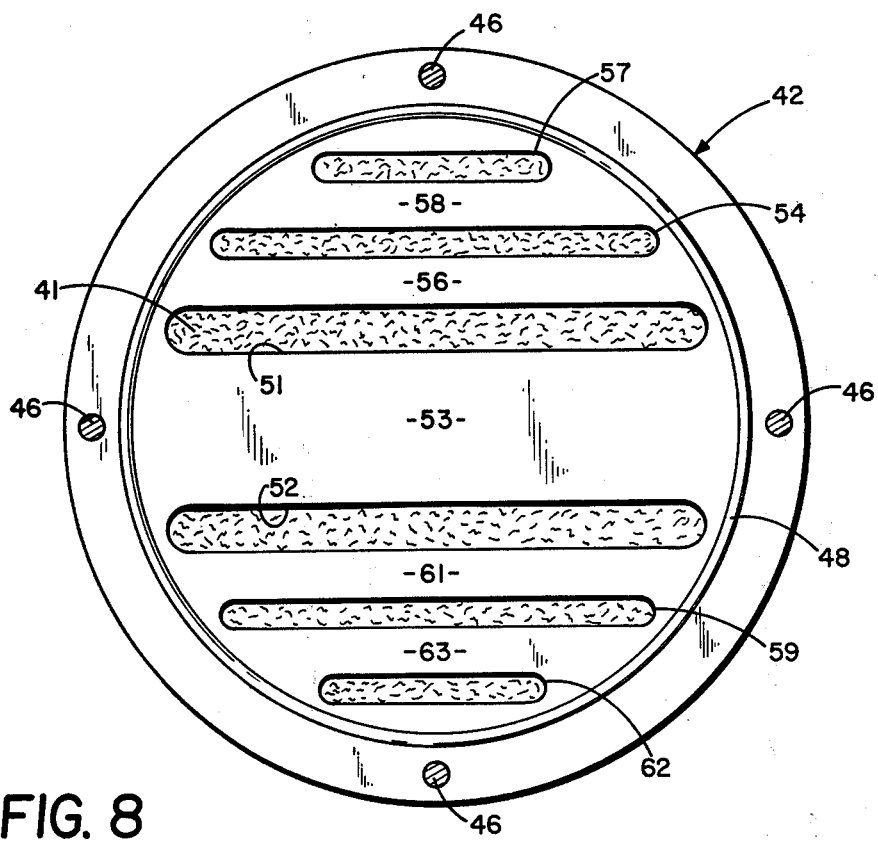

Referring to FIGS. 7 and 8, the upper surface of impactor plate 42 has a circular groove 48 accommodating an O-ring or annular seal 49. The lower surface of nozzle plate 43 rests on seal 49. Bolts 46 hold plate 43 in firm engagement with seal 49 so that all of the gas and aerosol must pass through the nozzles of nozzle plate 43.

As shown in FIG. 8, impactor plate 42 has a plurality of elongated linear slots 51, 52, 54, 57, 59, 62 providing passages through the plate. A pair of slots 51 and 52 are located adjacent opposite sides of a center rib or bridge 53. Bridge 53 extends along the horizontal diameter of plate 43. A slot 54 is spaced outwardly from slot 51 and forms therewith a second elongated rib or bridge 56. A further slot 57 is located laterally of slot 54 and forms therewith a third rib or bridge 58. The other half of plate 42 has similar slots. Slot 59 is spaced outwardly from slot 52 and forms therewith a rib or bridge 61. A further slot 62 spaced laterally of slot 59 forms with slot 59 a bridge or rib 63. Ribs 53, 56, 58, 61 and 63 extend parallel to each other and have flat smooth and continuous upper surfaces facing the bottom side of nozzle plate 43.

Referring to FIGS. 3, 4, 5 and 6, nozzle plate 43 comprises a circular metal disc 64 having an enlarged outer peripheral flange 66. Flange 66 has a flat inner surface locatable in surface engagement with the outer peripheral upper surface of impactor plate 42 and seal 49. Holes 44 extend through disc 64 and accommodate the connecting bolts 46. The inner surface of disc 64 has recesses 67 and 68 forming three chambers 69, 71 and 72. As shown in FIG. 4, chamber 69 is a central circular chamber. Chamber 71 is a rectangular chamber open to chamber 69 and extended diametrically across the third enlarged circular chamber 72. The axial dimension or depth of chambers 69, 71 and 72 vary. Chamber 69 has the greatest depth indicated as $S_1$, in FIG. 5. Chamber 71 has a depth $S_2$. Chamber 72 has the shortest depth indicated as $S_3$.

Disc 64 has a band or rib 73 projected upwardly from the top surface thereof and extended diametrically across the disc. An upwardly directed cylindrical boss 74 is integral with the center portion of rib 73. Boss 74 has a first opening or hole 76 leading to the center of chamber 69. The inlet end of hole 76 has a cone-shaped entrance 77.

A plurality of second openings or holes 78 are located in the rib 73 on opposite sides of boss 74. Holes 78 lead to chamber 71. The inlet ends of hole 78 have cone-shaped entrances 79. An equal number of holes 78 are located adjacent opposite sides of boss 74 as shown in FIGS. 3 and 4. Preferably, there are eight holes 78. The combined cross sectional areas of all of holes 78 equals the cross sectional area of hole 76.

A plurality of third openings or holes 81 are located on opposite sides of center rib 73. Holes 81 are located in rows aligned with ribs 56, 58, 61 and 63 of impactor plate 42. The exit ends of holes 81 open to chamber 72. The inlet end of each of the holes has a cone-shaped entrance 82. The outlet or inside ends of holes 76, 78 and 81 are spaced by the distances $S_1$, $S_2$ and $S_3$, from the impactor plate 42.

Figure 9:
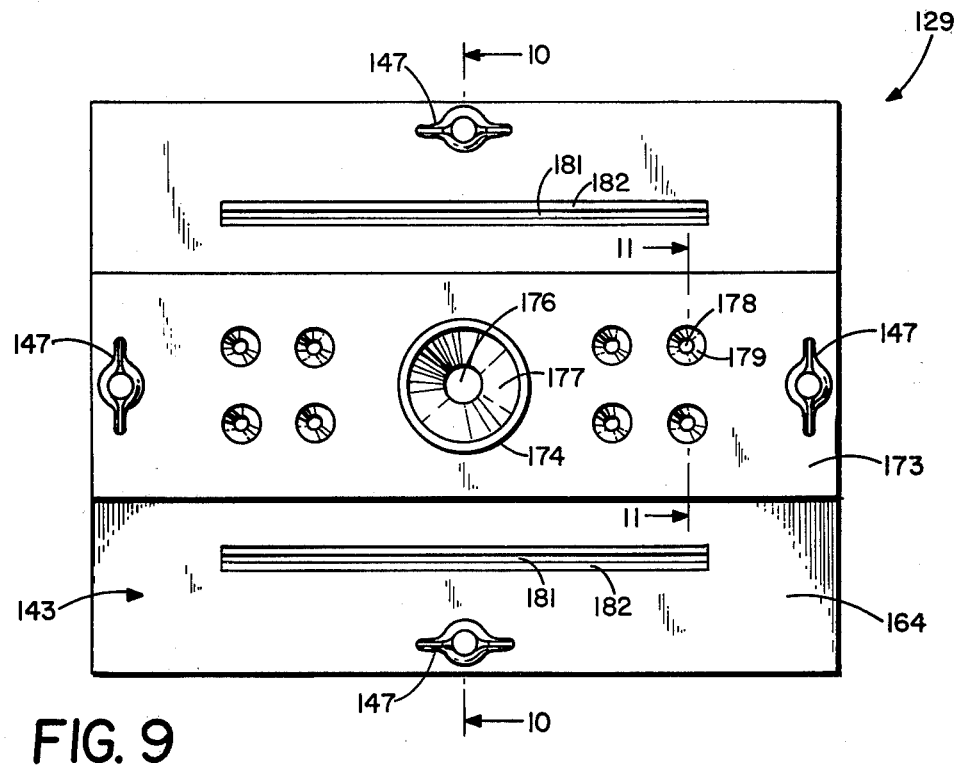
Figure 10:
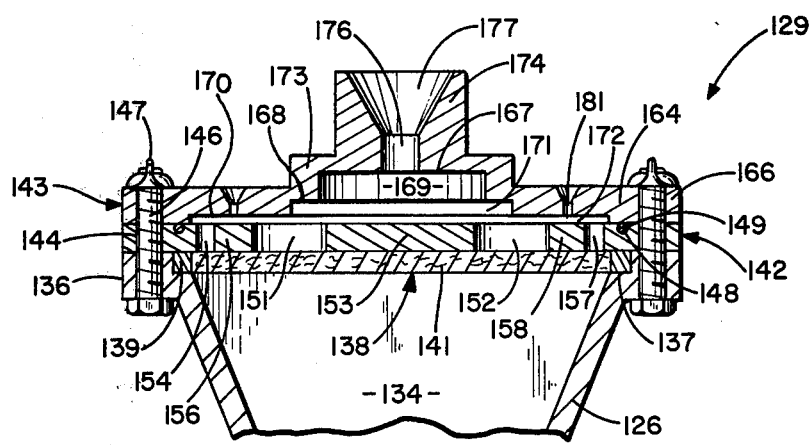
Figure 11:
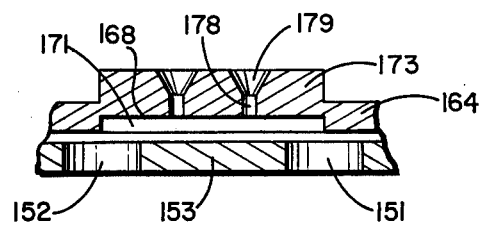

Referring to FIGS. 9–11, there is shown a modification of the impactor unit indicated generally at 129. Impactor 129 can be used with the sampler 24 in the high volume sampling apparatus 20. Impactor unit 129 has a funnel-shaped housing 126 having a passage 134 connected to the blower of the sampler. Housing 126 has an outside lip 136 having an inside shoulder 137.

A filter 138 rests on shoulder 137 to collect all of the particulates that pass through impactor plate 142. Filter 138 has an outside peripheral flange 139 resting on shoulder 137 and a filter media 141. Impactor plate 142 is located immediately above filter 138. The filter after the test is completed is analyzed to determine properties and chemistry of the collected particles. The analysis can be chemical, X-ray diffraction and weight. Other instruments in lieu of the filter can be used to measure the size, size distribution and amounts of particles that pass through the impactor plate. These instruments can be an aerosol mass monitor, optical particle counter, and cascade impactor.

A rectangular nozzle plate indicated generally at 143 is mounted on top of impactor plate 142. Nozzle plate 143, impactor plate 142, and lip 136 have a plurality of aligned holes 144 for accommodating bolts 146. Wing nuts 147 threaded on bolts 146 clamp the plates 142, 143 and lip 136 together.

Impactor plate 142 has a continuous groove 148 accommodating a seal 149. Nozzle plate 143 engages seal 149. Referring to FIG. 10, impactor plate 142 has a pair of slots 151 and 152 located on opposite sides of a center rib 153. Rib 153 extends along the longitudinal dimension of plate 142. A second pair of slots 154 and 157 are located along the opposite sides of plate 142. Slot 154 forms with slot 152 a second rib or bridge 156. Slot 157 forms with slot 152 a third rib or bridge 158.

The impactor plate 142 is a generally rectangular plate member 164 having an enlarged outer peripheral flange 166. The lower surface of flange 166 is flat and in engagement with the top of impactor plate 142 and seal 149. The inside surface of impactor plate 164 has three rectangular recesses 167, 168 and 170. Recess 167 is circular and forms a first cylindrical chamber 169. Recess 168 extends longitudinally across the center of the plate and forms second chamber 171. Recess 170 forms a third chamber 172 that has a generally rectangular shape and includes the lower portions of chambers 169 and 171.

An upwardly directed rib or member 173 extends longitudinally across the center of plate 164. An upwardly directed cylindrical boss 174 is located in the center of rib 173. Boss 174 has a first opening or hole 176 open to chamber 169. The entrance portion of hole 176 is a cone-shaped wall 177. Located on opposite sides of boss 174 are a plurality of second openings or holes 178 open to the chamber 171. The entrance portion of holes 178 have a cone-shaped wall 179. There are eight holes 178. The combined cross sectional areas of the eight holes 178 equals the cross sectional area of hole 176.

A pair of elongated third openings or slots 181 are located on opposite sides of rib 173. Slots 181 are open to chamber 172 and are in alignment with impactor plate ribs 156 and 158. The entrance portions of slots 181 have V-shaped walls 182. Slots 181 have a combined cross sectional area equal to the cross sectional area of hole 176.

Figure 12:
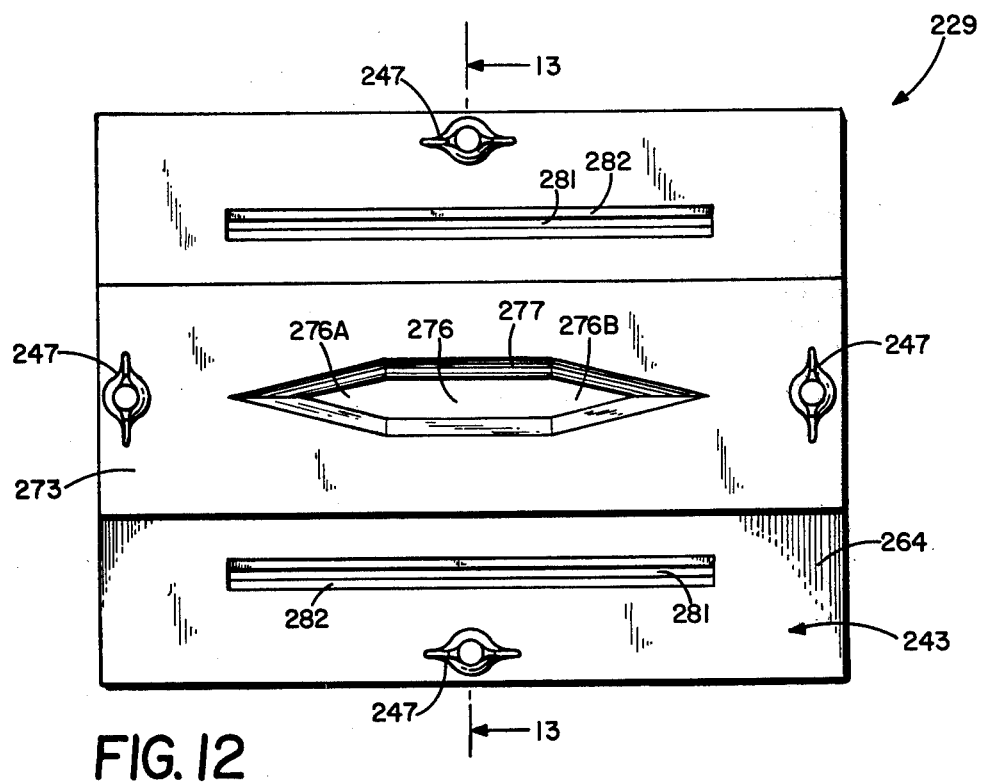
Figure 13:
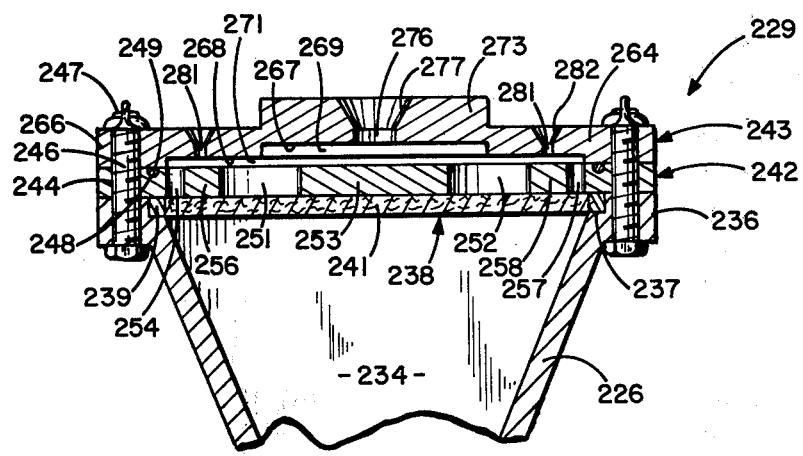

Referring to FIGS. 12 and 13, there is shown a further modification of the impactor unit indicated generally at 229 usable in the sampler 24 of the high volume sampling apparatus 20. Impactor 229 has a funnel-shaped housing 226 providng a passage 234 to the blower of sampler 24. Housing 226 has an upper outwardly directed lip 236 having an inside shoulder 237. A filter indicated generally at 238 is located on shoulder 237. Filter 238 has an outer peripheral frame 239 carrying a filter media 241. Filter media 241 extends across the open upper end of housing 226. The filter after the test is completed is analyzed to determine properties and chemistry of the collected particles. The analysis can be chemical, X-ray defraction and weight. Other instruments in lieu of the filter can be used to measure the size, size distribution and amounts of particles that pass through the impactor plate. These instruments can be an aerosol mass monitor, optical particle counter, and cascade impactor.

An impactor plate, indicated generally at 242, and nozzle plate 243 are mounted on top of flange 236 with a plurality of bolts 246. The bolts 246 extend through aligned holes 244 in plates 242 and 243 and wing nuts 247 on bolts clamp the plates 242 and 243 on lip 236. Impactor plate 242 has a groove accommodating a seal 249 that engages the lower surface of nozzle plate 243.

As shown in FIG. 13, impactor plate 242 has a pair of slots 251 and 252 located on opposite sides of a center rib or bridge 253. Rib 253 extends longitudinally along the center line of impactor plate 242. A pair of second slots 254 and 257 are located along the opposite sides of impactor plate 242. Slot 254 forms with slot 251 a second rib or bridge 256. Slot 257 forms with slot 252 a third rib or bridge 258.

Nozzle plate 243 is a rectangular, generally flat plate 264 having an enlarged outer peripheral flange 266. The lower surface of flange 266 is flat and in surface engagement with the upper surface of the outer peripheral edge of impactor plate 242 and seal 249. Plate 264 has a pair of upwardly directed recesses 267 and 268 forming two chambers 269 and 271. Chamber 269 is located under a transverse rib or member 273 and is open to a central opening, hole or slot 276. The entrance portion of slot 276 has V-shaped side walls 277. Slot 276 has triangular-shaped opposite ends 276A and 276B.

A pair of elongated second openings or slots 281 are located on opposite sides of the rib 273. Each slot 281 has an entrance opening having converging sides 282. Slots 281 are open to chamber 271 and are aligned with the ribs 256 and 258.

Referring to FIGS. 14–18, there is shown a fourth modification of the sampling instrument of the invention indicated generally at 324. Instrument 324 has five different size openings or slots providing the instrument with five distinct and different particle collection cut-off characteristics. The operating characteristics of instrument 324 are illustrated in the diagram of FIG. 21.

Instrument 324 has a housing 326 surrounding a passage 334 for carrying gases and particles to instrumentation for measuring particle size and particle concentrations. This instrumentation can include an aerosol mass monitor as disclosed in U.S. Pat. No. 3,561,253, an optical particle counter or a cascade impactor. A filter can be used to collect these particles.

Housing 326 has an outwardly directed lip or ledge 336 carrying an impactor unit indicated generally at 329. Lip 336 has an annular groove 337 accommodating a sealing ring or O-ring 338 engageable with the bottom of impaction plate 342.

Impactor unit 329 has an impactor plate 342 mounted on lip 336 and a nozzle plate 343 mounted on impactor plate 342. Plates 342 and 343 have aligned holes 344 accommodating a plurality of bolts 346. Wing nuts 347 threaded onto bolt 346 secure plates 342 and 343 in assembled relation with each other and lip 336. The top surface of plate 342 has an annular groove 348 accommodating a seal or O-ring 349. Ring 349 engages the bottom surface of nozzle plate 343. Seals 338 and 349 insure that all of the gas and particulates moving through the impactor unit 329 and housing 326 pass through the openings in nozzle plate 343.

Impactor plate 342 has a plurality of elongated passages separated by longitudinal ribs. A first pair of passages 351 and 352 are laterally separated from each other with a longitudinal rib 353. Rib 353 is recessed from the plane of the top surface of plate 342. The top of rib 353 has a flat generally horizontal surface. A second rib 356 extends from adjacent one side of slot 352 to a third slot 354/ Rib 356 is recessed below the horizontal plane of the top surface of plate 342 a distance less than the recess distance of rib 353. The top surface of rib 356 is flat. A pair of longitudinal ribs 358 and 361 are formed by longitudinal slots 354, 357, and 359. Each rib 358 and 361 has a flat top surface which is recessed a small distance below the horizontal plane of the top of plate 342. The recess positions of the plates 353, 356, 358 and 361 are shown in FIG. 15.

Figure 16:
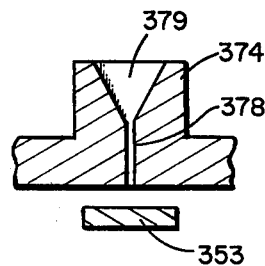

Impactor plate 342 has an upwardly directed transverse rib 372. Rib 372 has three step sections 373, 374 and 375. The first section 373 has a rectangular opening 376 having an exit aligned with the center of rib 353. The upper end or entrance of opening 376 is open to an upwardly diverging mouth 377. Second section 374 has a generally rectangular shaped opening 378 longitudinally aligned with opening 376. The exit end of opening 378 is aligned with the midsection of rib 353. As shown in FIG. 16, the upper end or entrance of opening 378 is open to an upwardly diverging mouth 379.

Figure 14:
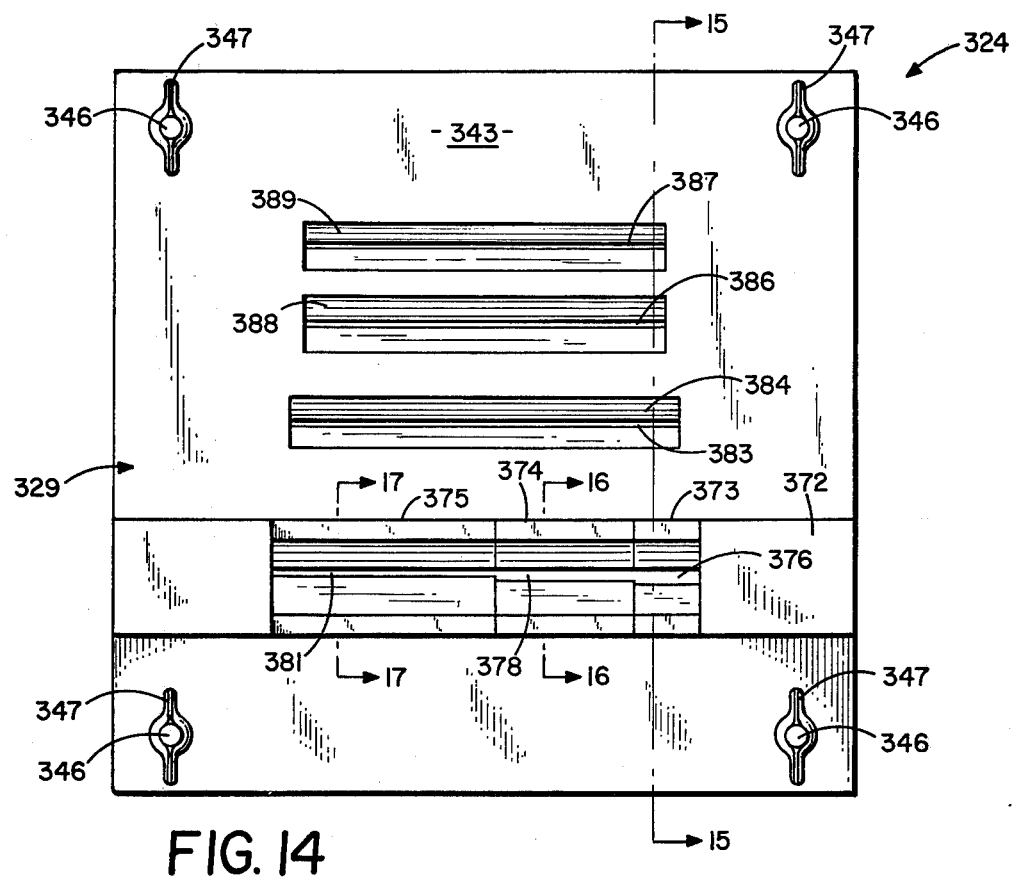
Figure 17:
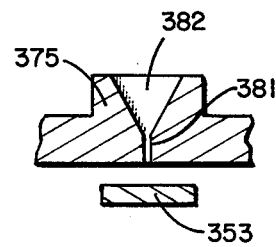
Figure 18:
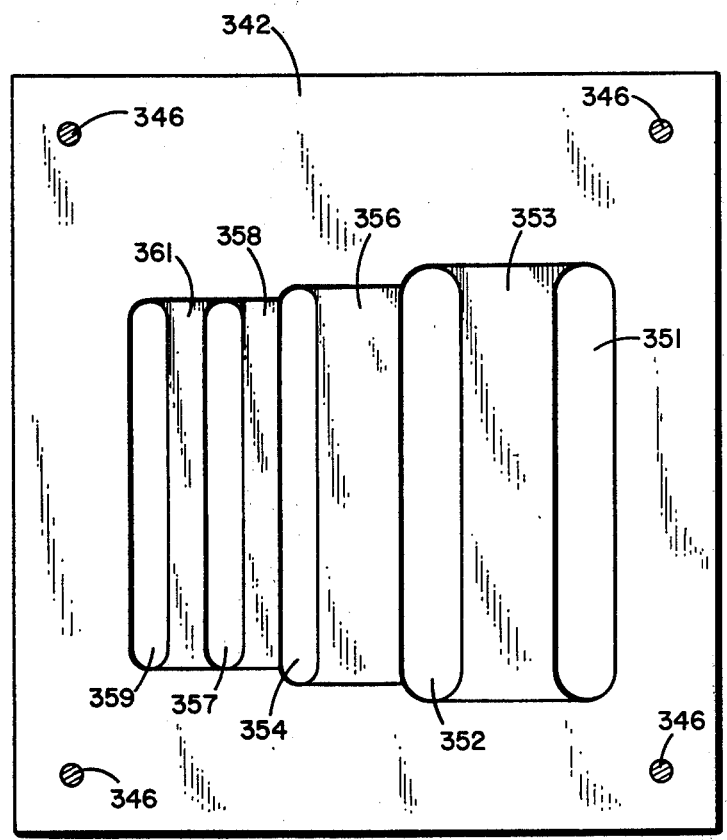

A third elongated rectangular opening 381 is located in the third section 375. Opening 381 is longitudinally aligned with openings 376, 378. The exit end of opening 381 is aligned with the rib 353 as shown in FIG. 17. The upper end or entrance of opening 381 is open to an outwardly diverging mouth 382. As shown in FIG. 14, the openings 376, 378 and 381 are decreasingly smaller in width and increase in length.

Figure 15:
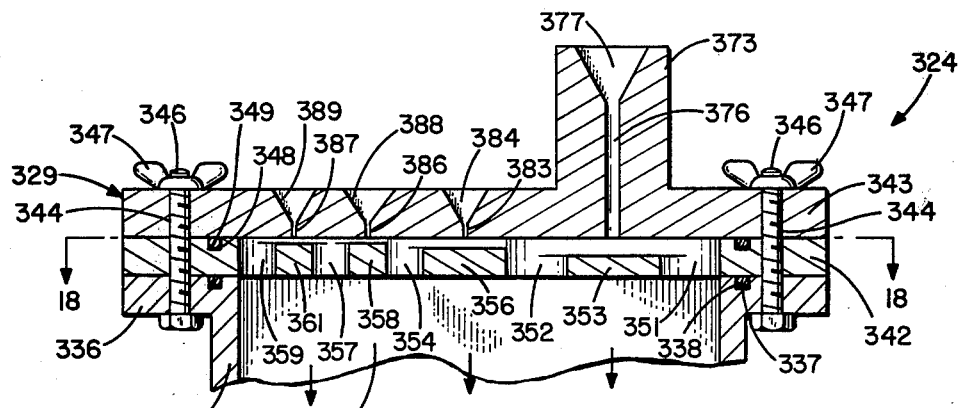

Referring to FIGS. 14 and 15, a fourth longitudinal generally rectangular opening 383 extends along the center portion of plate 343. The exit end of opening 383 is aligned with the center of rib 356. The inlet end or entrance of opening 383 is open to an upwardly diverging elongated mouth 384.

A pair of fifth openings 386 and 387 extend parallel to opening 383. The exit ends of the fifth openings 386 and 387 are open to the top surfaces of longitudinal ribs 358 and 361. The entrance end of opening 386 is open to an outwardly diverging mouth 388. A similar outwardly diverging longitudinal mouth 389 is open to the entrance end of opening 387.

The cross sectional area of the first opening 376, the second opening 378, the third opening 381, the fourth opening 386 and the combined cross sectional area of the fifth openings 386 and 387 are equal to each other. For example, the five opening sizes can be as follows: opening 376 — 0.22 cm × 1.0 cm; opening 378 — 0.10 cm × 2.3 cm; opening 381 — 0.060 cm × 3.8 cm; opening 386 — 0.035 cm × 6.5 cm; and openings 386 and 387 — 0.019 cm × combined length 12 cm. The flow of air and particulates through the nozzle plate 343 is divided into five cut-off sizes. The openings 376, 378, 383, 386 and 387 can have other cross sectional hole size relationships. The collection efficiency curve of impactor unit 329 as compared to a predetermined respirable curve is shown in FIG. 21.

The multiple nozzle plate of each modification of the impactor unit has a plurality of different sized openings or nozzles that have coordinated size differences so that the impactor unit will produce data that approximates one of the respirable penetration curves shown in FIG. 1. The openings or nozzles can be all round, all rectangular, or a combination of round and rectangular. Other shapes can be used for the openings. The degree to which the combined penetration curve of the impactor unit will approximate the selected respirable penetration curve is a function of the number of different cut-off sizes of the nozzles. Once the number of cut-off sizes of the nozzles has been selected, the value of the cut-off size and the fraction of the total flow which passes through each size nozzle must be determined. This determination is made by selecting either the cut-off sizes of the fraction of flow through each cut-off size and then determining the other parameter of the respirable penetration curve.

The pressure drop across the nozzles is the same for all nozzles. Thus the velocity of this air in each nozzle is the same and the cut-off size is governed by the size of the nozzles as in Equation 1. The relative total area of the different size nozzles is adjusted so that a predetermined collection efficiency curve is approximated in a stepwise fashion.

For any specific $\Delta$ P, and thus $V_o$, the cut-off size will be governed by W as expressed in Equation 1. The relative total area of the different size nozzles is adjusted so that a predetermined collection efficiency curve is approximated in a stepwise fashion.

The following example is directed to the impactor unit 29 as shown in FIGS. 2-8. Impactor unit 29 is a single stage impactor having three cut-off nozzle sizes. The operating characteristics of impactor unit 29 is shown in the diagram of FIG. 20. The fraction of the flow of air through the nozzles is equally divided among the three groups of nozzles 76, 78 and 81. Thus, one-third of the flow will pass through hole 76, one-third through holes 78, and one-third through holes 81. The cut-off size of the three groups of nozzles are representative of particle size in the penetration ranges of 0% to 33⅓%, 33⅓% to 66⅔%, and 66⅔% to 100%. When the cut-off sizes are chosen at the midpoint of these ranges, the sizes are 2.2 μm, 3.5 μm, and 5.8 μm aerodynamic diameter. The hole diameter 76 with a ⅓ cfm flow rate is 0.58 cm. The diameters of the holes 78 and 81 are 0.21 cm and 0.086 cm, respectively. There are eight holes with 0.21 cm diameter and 45 holes with 0.086 cm diameter.

In use, blower 27 is operated to draw air through the passage 34 of casing 26. The air is drawn through holes 76, 78 and 81 in nozzle plate 43. The pressure drop across the holes 76, 78 and 81 is the same so that the average velocity of the air in the holes is the same. The average velocity is the flow rate divided by the nozzle area. Aerosol particles larger than 2.2 μm aerodynamic diameter are collected on the collection surfaces of ribs 56, 58, 61 and 63. The collection surface of rib 53 is used to collect particles larger than 3.5 μm aerodynamic diameter discharged from nozzle openings 78. The middle of collection surface of rib 53 accommodates particles larger than 5.8 μm aerodynamic diameter discharge from opening 76. All the particles that are not collected on the ribs 53, 56, 58, 61 and 63 are collected on filter 38. The filter after the test is completed is analyzed to determine properties and chemistry of the collected particles. The analysis can be chemical, X-ray diffraction and weight. Other instruments in lieu of the filter can be used to measure the size, size distribution and amounts of particles that pass through the impactor plate. These instruments can be an aerosol mass monitor, optical particle counter, and cascade impactor.

Nozzle dimensions for both round and rectangular nozzles of a respirable impactor with three cut-off sizes (n = 3) operating at a total flow rate of $Q_t = 28.3$ 1pm (ca. 1 cfm) can be determined as follows: In all calculations, air viscosity and density and particle density is assumed to be $\mu = 1.81 \times 10^{-4}$ poise, $p = 1.2 \times 10-3$ g/cm³ and $\rho_p = 1$ g/cm³, respectively. Round Nozzles:

To minimize the number of nozzles, a single nozzle is used for the classification of the largest particles. Since $V_o = Q_t/n/\pi W_{RD_1}{}^{2/4}$, $$V_o = \frac{Q_t/n}{\pi W_{RD_1}{}^{2/4}}, \qquad \text{(A-1)}$$

the nozzle diameter, $W_{RD_1}$ is found from equation 1 to be $$W_{RD_1} = \left[ \frac{4 \rho_p C Q_t/n D_{P50}{}^2}{9\pi \mu Stk_{50}} \right]^{\frac{1}{2}} \qquad \text{(A-2)}$$

with C = 1.03 (1 atmospheric pressure), $D_{P50} = 5.8$ μm and the $\sqrt{Stk_{50}} = 0.47$. It is found from equation A-2, that $W_{RD} = 0.58$ cm. The corresponding average velocity of the air in the nozzle is found to be $V_o = 595$ cm/sec. To check the value of $\sqrt{Stk_{50}}$, Re must be calculated. From Equation 2, it is found that Re = 2300 and the choice of $\sqrt{Stk_{50}} = 0.47$ is satisfactory, as set out in the Marple and Liu publication.

Since the pressure drop will be the same for all nozzles, Equation 4 shows that $V_o$ will be the same. Therefore, from Equation 1 for $D_{P50} = 3.5$ μm, C = 1.04 and $\sqrt{Stk_{50}} = 0.47$, it will be found that $W_{RD_2} = 0.21$ cm. The number of nozzles, $N_2$, to pass a flow rate of $Q_T/n$ at an average velocity of $V_o$ is found from the equation $$N_i = \frac{Q_T/n}{V_o \pi W_{RD_i}^2/4} \qquad (5)$$

to be 7.6. Since the number of nozzles must be an even integer, eight nozzles are used. The Reynolds number for Equation 2 will be Re = 830 and $\sqrt{Stk_{50}} = 0.47$ is seen from the above Marple and Liu publication to be satisfactory.

In like manner for the smallest set of nozzles, where $D_{P50} = 2.2$ μm, C = 1.07 and $\sqrt{Stk_{50}} = 0.47$ it will be found that $W_{RD_3} = 0.086$, $N_3 = 45$ and Re = 340. Again, the Marple and Liu publication shows $\sqrt{Stk_{50}} = 0.47$ is satisfactory. Rectangular Nozzles:

Rectangular nozzle impactors can be substituted for any corresponding set of round nozzles. In this analysis it will be assumed that the discharge coefficients are the same for both the round and rectangular nozzles. Also, since the pressure drop will be the same for all nozzles, $V_o$ through all nozzles will be the same.

From Equations 1, 2 and 3, the following relationships will be found for round and rectangular nozzles with the same cut-off size, $D_{P_{50}}$:

$$W_{Rect} = W_{RD} \frac{Stk_{50_{RD}}}{Stk_{50_{Rect}}} \quad (6)$$

and $$Re_{Rect} = 2 \, Re_{RD} \frac{W_{Rect}}{W_{RD}} \quad (7)$$

the nozzle length can be found from:

$$L = \frac{Q_T/n}{V_o W_{Rect}} \quad (8)$$

By using these equations, the values of W, Re, and L for the rectangular nozzles were found. The values for this example case are given in Table I for one, three and five cut-off sizes.

Table I

Round and Rectangular Nozzle Dimensions for Respirable Impactors at 28.3 1pm (1 cfm) Flow Rate

| | | Round | | | | Rectangular | | | |
|---|---|---|---|---|---|---|---|---|---|
| Number of cut-off sizes, n | Cut-off size, $D_{P50}$ (μm) | $\sqrt{Stk_{50}}$ | Nozzle Diam., $W_R$(cm) | Number of Nozzles, N | Re | $\sqrt{Stk_{50}}$ | Nozzle Width, $W_{Rect}$(cm) | Nozzle Length, L(cm) | Re |
| 1 | 3.5 | 0.46 | 0.61 | 1 | 6,500 | 0.73 | 0.24 | 1.2 | 5,100 |
| | 5.8 | 0.47 | 0.58 | 1 | 2,300 | 0.73 | 0.24 | 1.1 | 1,900 |
| 3 | 3.5 | 0.47 | 0.21 | 8 | 830 | 0.74 | 0.085 | 3.1 | 670 |
| | 2.2 | 0.47 | 0.086 | 45 | 340 | 0.74 | 0.035 | 7.5 | 280 |
| | 6.7 | 0.47 | 0.54 | 1 | 1,500 | 0.73 | 0.22 | 1.0 | 1,200 |
| | 4.6 | 0.47 | 09.25 | 5 | 680 | 0.74 | 0.10 | 2.3 | 540 |
| 5 | 3.5 | 0.47 | 0.15 | 13 | 410 | 0.74 | 0.060 | 3.8 | 330 |
| | 2.7 | 0.47 | 0.088 | 38 | 240 | 0.75 | 0.035 | 6.5 | 190 |
| | 2.0 | 0.47 | 0.049 | 121 | 130 | 0.76 | 0.019 | 12 | 100 |

The impactor unit can have a mix of round and rectangular nozzles as disclosed in FIGS. 9–11. For example, it may be desirable to substitute a single rectangular nozzle for the forty-five 0.086 cm diameter nozzles. In this case, the value of $V_o = 595$ cm/sec and Equation 1 will give a jet-width of 0.035 cm. The length will have to be 7.5 cm to accommodate a flow rate of 9.4 lpm. In like manner, a slot of 0.085 cm × 3.1 cm could be used instead of the eight 0.21 cm diameter nozzles. Also, the corresponding slot size for the 0.58 cm diameter nozzle is 0.24 cm × 1.1 cm.

The respirable impactor units can be made with different flow rates or different number of cut sizes. The degree to which the penetration curves of these impactors approach the respirable penetration curve is shown in FIGS. 20 and 21. This shows that agreement is improved as the number of cut-off sizes increases.

The several embodiments of the impactor unit are examples of the impactor unit of the invention. Modification, changes in parts and materials, and nozzle sizes and groupings can be made by those skilled in the art within the scope of the invention. The invention is defined in the following claims.

The embodiments of the invention in which an exclusive property or privilege is claimed are defined as follows:

1. A single stage impactor unit having a particle collection efficiency curve that approximates a predetermined curve comprising: particle collecting means having at least one surface for collecting particles and at least one passage located adjacent said surface allowing particles to move through the collecting means, and impactor means having a plurality of separate openings aligned with said surface for directing particles toward said surface, said openings having at least two different cross sectional areas and wherein the total cross-sectional areas of all openings of each size are substantially equal, whereby when gas and particles are moved through said openings, with the same pressure drop across the openings, particles of a particle size range related to the size of each opening moving through each opening are collected on said surface so that the combined particle collection efficiency curve of all the openings approximates a predetermined curve.

2. The unit of claim 1 wherein: the openings are round holes.

3. The unit of claim 1 wherein: the openings comprise at least a first opening, second openings and third openings.

4. The unit of claim 1 wherein: each opening is determined by the equation:

$$D_{P50} = \left[ \frac{9\mu\, W\, Stk_{50}}{\rho_p\, C\, V_o} \right]^{\frac{1}{2}}$$

where $\mu$ = air viscosity

W = nozzle diameter (round impactor) or nozzle width (rectangular impactor)

$Stk_{50}$ = Stokes number corresponding to 50% particle collection

C = Cunningham slip correction $V_o$ = average velocity in nozzle = flow rate/nozzle area.

5. The unit of claim 1 including: means for collecting the particles that move through the collecting means.

6. A single stage impactor unit having a particle collection efficiency that approximates a predetermined curve comprising: particle collecting means having at least one surface for collecting particles and at least one passage allowing particles to move through the collecting means, and impactor means having a plurality of separate openings aligned with said surface for directing particles towards said surface, said openings comprising at least a first opening, second openings, and third openings, said openings having different cross sectional areas, the cross sectional areas of the first opening and second and third openings are equal to each other, whereby when gas and particles are moved through said openings, particles of a particle size range related to the size of each opening moving through each opening are collected on said surface so that the combined particle collection efficiency curve of all of the openings approximates a predetermined curve.

7. The unit of claim 6 wherein: the openings are round holes.

8. The unit of claim 6 wherein: the third openings have generally rectangular cross sectional areas.

9. The unit of claim 6 wherein: some of the openings have generally rectangular cross sectional areas.

10. The unit of claim 6 wherein: the particle collecting means is a plate having passages and ribs separated by the passages, said ribs having a surface for collecting particles.

11. The unit of claim 6 wherein: each opening is determined by the equation:

$$D_{P_{50}} = \left[ \frac{9\mu \, W \, Stk_{50}}{\rho_p \, C \, V_o} \right]^{\frac{1}{2}}$$

where
$\mu$ = air viscosity
$W$ = nozzle diameter (round impactor) or nozzle width (rectangular impactor)
$Stk_{50}$ = Stokes number corresponding to 50% particle collection.
$C$ = Cunningham slip correction
$V_o$ = average velocity in nozzle = flow rate/nozzle area.

12. A single stage impactor unit having a particle collection efficiency curve that approximates a predetermined curve comprising: particle collecting means having at least one surface for collecting particles and at least one passage allowing particles to move through the collecting means, and impactor means having a plurality of separate openings aligned with said surface for directing particles towards said surface, said openings comprising at least a first opening, second openings, and third openings, said openings having different cross sectional areas, the cross sectional area of the first opening is equal to the cross sectional area of the second openings, whereby when gas and particles are moved through said openings particles of a particle size range related to the size of each opening moving through each opening are collected on said surface so that the combined particle collection efficiency curve of all of the openings approximates a predetermined curve.

13. The unit of claim 12 wherein: all the openings are round holes.

14. The unit of claim 12 wherein: the third openings have generally rectangular cross sectional areas.

15. The unit of claim 12 wherein: some of the openings have generally rectangular cross sectional areas.

16. The unit of claim 12 wherein: the particle collecting means is a plate having passages and ribs separated by the passages, said ribs having said surface for collecting particles.

17. The unit of claim 12 wherein: each opening is determined by the equation:

$$D_{P_{50}} = \left[ \frac{9\mu \, W \, Stk_{50}}{\rho_p \, C \, V_o} \right]^{\frac{1}{2}}$$

where
$\mu$ = air viscosity
$W$ = nozzle diameter (round impactor) or nozzle width Rectangular impactor)
$Stk_{50}$ = Stokes number corresponding to 50% particle collection
$C$ = Cunningham slip correction
$V_o$ = average velocity in nozzle = flow rate/nozzle area.

18. A single stage impactor unit having a particle collection efficiency curve that approximates a predetermined curve comprising: particle collecting means having at least one surface for collecting particles and at least one passage allowing particles to move through the collecting means, said particle collecting means comprising a plate having passages and ribs separated by the passages, said ribs having said surface for collecting particles, and impactor means having a plurality of separate openings aligned with said surface for directing particles toward said surface, said openings having different cross sectional areas, whereby when gas and particles are moved through said openings particles of a particle size range related to the size of each opening moving through each opening are collected on said surface so that the combined particle collection efficiency curve of all of the openings approximates a predetermined curve.

19. The unit of claim 18 including: means operable to move gas and particles through said openings.

20. The unit of claim 18 wherein: the openings are round holes.

21. The unit of claim 18 wherein: some of the openings have generally rectangular cross sectional areas.

22. The unit of claim 18 wherein: each opening is determined by the equation:

$$D_{P_{50}} = \left[ \frac{9\mu \, W \, Stk_{50}}{\rho_p \, C \, V_o} \right]^{\frac{1}{2}}$$

where
$\mu$ = air viscosity
$W$ = nozzle diameter (round impactor) or nozzle width (rectangular impactor)
$Stk_{50}$ = Stokes number corresponding to 50% particle collection
$C$ = Cunningham slip correction
$V_o$ = average velocity in nozzle = flow rate/nozzle area.

23. The unit of claim 18 wherein: the openings comprise a first opening, a second opening, a third opening, a fourth opening, and fifth openings.

24. The unit of claim 23 wherein: all the openings are elongated rectangular slots.

25. A single stage impactor unit having a particle collection efficiency curve that approximates a predetermined curve comprising: particle collecting means having at least one surface for collecting particles and at least one passage allowing particles to move through the collecting means, and impactor means having a plurality of separate openings aligned with said surface for directing particles toward said surface, said openings comprising a first opening, a second opening, a third opening, a fourth opening, and fifth openings, said openings having different cross sectional areas, the cross sectional areas of each of the first, second, third, fourth and fifth openings are substantially equal to each other, whereby when gas and particles are moved through said openings particles of a particle size range relating to the size of each opening moving through each opening are collected on said surface so that the combined particle collection efficiency curve of all of the openings approximates a predetermined curve.

26. The unit of claim 25 wherein: all of the openings are round holes.

27. The unit of claim 25 wherein: some of the openings have generally rectangular cross sectional areas.

28. The unit of claim 25 wherein: all of the openings are elongated rectangular slots.

29. The unit of claim 25 wherein: the particle collecting means is a plate having passages and ribs separated by the passages, said ribs having a surface for collecting particles.

30. The unit of claim 25 wherein: each opening is determined by the equation:

$$D_{P_{50}} = \left[ \frac{9\mu\, W\, Stk_{50}}{\rho_p\, C\, V_o} \right]^{\frac{1}{2}}$$

where
$\mu$ = air viscosity
$W$ = nozzle diameter (round impactor) or nozzle width (rectangular impactor)
$Stk_{50}$ = Stokes number corresponding to 50% particle collection
$C$ = Cunningham slip correction
$V_o$ = average velocity in nozzle = flow rate/nozzle area.

31. A single stage impactor unit having a particle collection efficiency curve that approximates a predetermined curve comprising: particle collecting means having a plurality of surfaces for collecting particles and passages separating the surfaces, allowing air and particles to move through the passages of the collecting means between said surfaces, impactor means having a plurality of separate openings aligned with said surfaces for directing particles toward said surfaces, said openings having different cross sectional areas whereby when air and particles are moved through all the openings, with the same pressure drop across the openings, particles of a size range related to the size of each opening moving through each opening are collected on said surfaces so that the combined particle collection efficiency curve of all the openings approximates a predetermined curve.

32. The unit of claim 31 wherein: the openings are round holes.

33. The unit of claim 31 wherein: the openings comprise at least a first opening, second openings and third openings.

34. The unit of claim 33 wherein: the cross sectional areas of the first opening and second and third openings are equal to each other.

35. The unit of claim 33 wherein: the cross sectional area of the first opening is equal to the cross sectional area of the second openings.

36. The unit of claim 33 wherein: all the openings are round holes.

37. The unit of claim 33 wherein: the third openings have generally rectangular cross sectional areas.

38. The unit of claim 31 wherein: some of the openings have generally rectangular cross sectional areas.

39. The unit of claim 31 wherein: the openings comprise a first opening, a second opening, a third opening, a fourth opening, and fifth openings.

40. The unit of claim 39 wherein: all the openings are elongated rectangular slots.

41. The unit of claim 39 wherein: the cross sectional areas of each of the first, second, third, fourth and fifth openings are substantially equal to each other.

42. The unit of claim 31 wherein: each opening is determined by the equation:

$$D_{P_{50}} = \left[ \frac{9\mu\, W\, Stk_{50}}{\rho_p\, C\, V_o} \right]^{\frac{1}{2}}$$

where
$\mu$ = air viscosity
$W$ = nozzle diameter (round impactor) or nozzle width (rectangular impactor)
$Stk_{50}$ = Stokes number corresponding to 50% particle collection
$C$ = Cunningham slip correction
$V_o$ = average velocity in nozzle = flow rate/nozzle area.

43. The unit of claim 32 including: means for collecting the particles that move through the collecting means.

44. A single stage impactor unit having a particle collection efficiency curve that approximates a predetermined curve comprising: particle collection means having a plurality of surfaces for collecting particles and passages allowing air and particles to move through the collection means, said particle collecting means comprising a plate having passages and ribs separated by the passages, said ribs having said surface for collecting particles, impactor means having a plurality of separate openings aligned with said surfaces for directing particles toward said surfaces, said openings having different cross sectional areas, whereby when air and particles are moved through all of the openings particles of a size range related to the size of each opening moving through each opening are collected on said surfaces so that the combined particle collection efficiency curve of all of the openings approximates a predetermined curve.

45. The unit of claim 44 wherein: the openings are round holes.

46. The unit of claim 44 wherein: the openings comprise at least a first opening, second openings and third openings.

47. The unit of claim 46 wherein: the cross sectional areas of the first opening and second and third openings are equal to each other.

48. The unit of claim 46 wherein: the cross sectional area of the first opening is equal to the cross sectional area of the second openings.

49. The unit of claim 46 wherein: all the openings are round holes.

50. The unit of claim 46 wherein: the third openings have generally rectangular cross sectional areas.

51. The unit of claim 44 wherein: some of the openings have generally rectangular cross sectional areas.

52. The unit of claim 44 wherein: the openings comprise a first opening, a second opening, a third opening, a fourth opening, and fifth openings.

53. The unit of claim 52 wherein: all the openings are elongated rectangular slots.

54. The unit of claim 52 wherein: the cross sectional areas of each of the first, second, third, fourth and fifth openings are substantially equal to each other.

55. The units of claim 44 wherein: each opening is determined by the equation:

$$D_{P_{50}} = \left[ \frac{9\mu\, W\, Stk_{50}}{\rho_p\, C\, V_o} \right]^{\frac{1}{2}}$$

where
$\mu$ = air viscosity
W = nozzle diameter (round impactor) or nozzle width (rectangular impactor)
$Stk_{50}$ = Stokes number corresponding to 50% particle collection
C = Cunningham slip correction
$V_o$ = average velocity in nozzle = flow rate/nozzle area.

56. The unit of claim 44 including: means for collecting the particles that move through the collecting means.

57. A single stage impactor unit having a collection efficiency curve that approximates a respirable penetration curve used with a casing having an open inlet end and a passage for carrying air, means operable to move air through said passage, and means for collecting particles that penetrate the impactor unit, comprising: an impactor plate having particle collecting members and a plurality of passages separated by said particle collecting members, a nozzle plate located over the impactor plate, said nozzle plate having a plurality of openings aligned with the particle collecting members of the impactor plate for directing particles toward said collecting members, said openings having different cross sectional areas whereby when air and particles are moved through said openings, with the same pressure drop across the openings, particles of a particle size range related to the size of each opening moving through each opening are collected on said collecting members so that the combined collection efficiency curve of all the openings approximates the respirable penetration curve.

58. The unit of claim 57 wherein: said nozzle plate has recesses defining chambers in communication with the openings and passages of the impactor plate.

59. The unit of claim 57 wherein: the impactor plate is a disc having a first rib extended across the diameter of the disc, and additional ribs located generally parallel to the first rib.

60. The unit of claim 57 wherein: the impactor plate has a first member extended along the midsection of the plate, and additional members located generally parallel to the first member.

61. The unit of claim 57 wherein: the openings in the nozzle plate are round holes.

62. The unit of claim 61 wherein: the holes comprise a first hole, second holes, and third holes.

63. The unit of claim 62 wherein: the cross sectional area of the first hole equals the total cross sectional areas of the second holes.

64. The unit of claim 62 wherein: the cross sectional area of the first hole equals the total cross sectional areas of the third holes.

65. The unit of claim 62 wherein: the cross sectional area of the first hole equals the total cross sectional area of the second holes and equals the total cross sectional area of the third holes.

66. The unit of claim 57 wherein: the openings in the nozzle plate comprise a first opening, second openings, and third openings having different cross sectional areas providing different particle collection cut-off characteristics.

67. The unit of claim 66 wherein: the first opening has a cross sectional area that equals the total cross sectional areas of the second openings.

68. The unit of claim 66 wherein: the first opening has a cross sectional area that equals the total cross sectional areas of the third openings.

69. The unit of claim 66 wherein: the first opening has a cross sectional area that equals the total cross sectional areas of the second openings and equals the total cross sectional areas of the third openings.

70. The unit of claim 66 wherein: at least one of said first, second or third openings is an elongated slit opening.

71. The unit of claim 66 wherein: the third openings comprise a pair of elongated slit openings.

72. The unit of claim 66 wherein: the first opening has an elongated rectangular shape, said second openings having a triangular shape and joined to the ends of the first opening, said third openings comprising elongated linear slit openings.

73. The unit of claim 57 wherein: the openings comprise a first opening, a second opening, a third opening, a fourth opening, and fifth openings.

74. The unit of claim 73 wherein: all the openings are elongated rectangular slots.

75. The unit of claim 73 wherein: the cross sectional areas of each of the first, second, third, fourth and fifth openings are substantially equal to each other.

76. The unit of claim 73 wherein: each opening is determined by the equation:

$$D_{P50} = \left[ \frac{9\mu\, W\, Stk_{50}}{\rho_p\, C\, V_o} \right]^{\frac{1}{2}}$$

where $\mu$ = air viscosity

W = nozzle diameter (round impactor) or nozzle width (rectangular impactor)

$Stk_{50}$ = Stokes number corresponding to 50% particle collection

C = Cunningham slip correction $V_o$ = average velocity in nozzle = flow rate/nozzle area.

77. A single stage impactor unit having a collection efficiency curve that approximates a respirable area penetration curve used with a casing having an open inlet end and a passage for carrying air, means operable to move air through said passage, and means for collecting particles that penetrate the impactor units, comprising: an impactor plate having particle collecting members and a plurality of passages separated by said particle collecting members, said impactor plate having elongated slots forming the passages and said particle collecting members comprising ribs separated by the slots, nozzle plate located over the impactor plate, said nozzle plate having a plurality of openings aligned with the particle collecting members of the impactor plate for directing particles toward said collecting members, said openings having different cross sectional areas, whereby when air and particles are moved through said openings, particles of a particle size range relating to the size of each opening moving through each opening are collected on said collecting members os that the combined collection efficiency curve of all the openings approximates the respirable penetration curve.

78. The unit of claim 77 wherein: the openings in the nozzle plate are round holes, said holes comprising a first hole, second holes, and third holes.

79. The unit of claim 78 wherein: the cross sectional area of the first hole equals the total cross sectional areas of the second holes.

80. The unit of claim 77 wherein: the openings in the nozzle plate comprise a first opening, second openings, and third openings having different cross sectional areas providing different particle collection cut-off characteristics.

81. The unit of claim 80 wherein: the first opening has a cross sectional area that equals the total cross sectional areas of the second openings.

82. The unit of claim 80 wherein: the first opening has a cross sectional area that equals the total cross sectional areas of the third openings.

83. The unit of claim 80 wherein: the first opening has a cross sectional area that equals the total cross sectional areas of the second openings and equals the total cross sectional areas of the third openings.

84. The unit of claim 80 wherein: at least one of said first, second or third openings is an elongated slit opening.

85. The unit of claim 80 wherein: the third openings comprise a pair of elongated slit openings.

86. The unit of claim 80 wherein: the first opening has an elongated rectangular shape, said second openings having a triangular shape and joined to the ends of the first opening, said third openings comprising elongated linear slit openings.

87. The unit of claim 77 wherein: the openings comprise a first opening, a second opening, a third opening, a fourth opening, and fifth openings.

88. The unit of claim 87 wherein: all the openings are elongated rectangular slots.

89. The unit of claim 87 wherein: the cross sectional areas of each of the first, second, third, fourth and fifth openings are substantially equal to each other.

90. The unit of claim 87 wherein: each opening is determined by the equation:

$$D_{P_{50}} = \left[ \frac{9\mu \, W \, Stk_{50}}{\rho_p \, C \, V_o} \right]^{\frac{1}{2}}$$

where
$\mu$ = air viscosity
$W$ = nozzle diameter (round impactor) or nozzle width (rectangular impactor)
$Stk_{50}$ = Stokes number corresponding to 50% particle collection
$C$ = Cunningham slip correction
$V_o$ = average velocity in nozzle = flow rate/nozzle area.

* * * * *

UNITED STATES PATENT AND TRADEMARK OFFICE
CERTIFICATE OF CORRECTION

PATENT NO. : 4,133,202
DATED : January 9, 1979
INVENTOR(S) : Virgil A. Marple

It is certified that error appears in the above-identified patent and that said Letters Patent are hereby corrected as shown below:

Column 8, line 17, "354/" should be --354.--.

Column 8, line 68, after "378" and before "383", insert --381--.

Column 10, line 15, "10--3" should be --$10^{-3}$--.

Column 10, line 19, omit equation which is repeated on line 20.

Column 10, line 34, "$\checkmark STK_{50}$" should be --$\sqrt{STK_{50}}$--.

Column 11, Table I, under column entitled "Nozzle Diameter $W_R$ (cm)", line 6, "09.25" should be --0.25--.

Column 18, line 66, "os" should be --so--.

Signed and Sealed this

Twenty-fourth Day of June 1980

[SEAL]

Attest:

SIDNEY A. DIAMOND

Attesting Officer

Commissioner of Patents and Trademarks